(12) United States Patent
Kumar et al.

(10) Patent No.: US 6,406,882 B1
(45) Date of Patent: Jun. 18, 2002

(54) IMMOBILIZED MICROBIAL CONSORTIUM FOR THE TREATMENT OF PHENOLIC WASTE-WATER FROM PETROLEUM REFINERIES

(75) Inventors: Rita Kumar; Alka Sharma; Archana Kumar, all of Delhi (IN)

(73) Assignee: Council for Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/537,441

(22) Filed: Mar. 27, 2000

(51) Int. Cl.[7] .................. C12N 11/02; C12N 11/12; C12P 39/00; C10G 32/00
(52) U.S. Cl. .................. 435/42; 435/178; 435/179; 435/281
(58) Field of Search .................. 435/42, 179, 281, 435/178

(56) References Cited

FOREIGN PATENT DOCUMENTS

| | | |
|---|---|---|
| EP | 0756002 | 1/1997 |
| JP | 9075971 | 3/1997 |
| JP | 9100187 | 4/1997 |
| WO | 9001465 | 2/1990 |

OTHER PUBLICATIONS

WPI English Abstract of JP 9100187 Dated Apr. 15, 1997.
WPI English Abstract of JP 9075971 Dated Mar. 25, 1997.

*Primary Examiner*—Herbert J. Lilling
(74) *Attorney, Agent, or Firm*—Ladas & Parry

(57) ABSTRACT

An immobilized microbial consortium is formulated which comprises of a synergistic mixture of all the bacterial strains of *Aeromonas hydrophila, Pseudomonas fluorescens, Pseudomonas aeruginosa, Bacillus circulans, Yersinia enterocolitica, Enterobacter cloaca* and *Bacillus brevis*. The formulated microbial consortium is immobilized on a non-biodegradable and economically cheaper support. The said immobilized microbial consortium is used for the biodegradation of synthetic phenol as well as phenol present in petroleum refinery effluent. The results of biodegradation obtained with the microbial consortium immobilized on coconut fiber are compared with those obtained with microbial consortium immobilized on well known support. The coconut fiber used for immobilization proved to be a better support than a well known support such as calcium alginate.

13 Claims, No Drawings

IMMOBILIZED MICROBIAL CONSORTIUM FOR THE TREATMENT OF PHENOLIC WASTE-WATER FROM PETROLEUM REFINERIES

FIELD OF THE INVENTION

The present invention relates to an immobilized microbial consortium and a process for the preparation of the said microbial consortium useful for the treatment of phenolic waste-water.

DESCRIPTION OF THE PRIOR ART

Phenols are hydroxy derivatives of benzene which originate both from anthropogenic sources such as forest fire, decay of lignocellulosic materials as well as from various human activities which originate from pharmaceutical industries, pesticide industries, petroleum refineries and wood processing industries.

In petroleum refineries, crude petroleum passes through various stages of refining before it is finally used as a fuel. The effluent of petroleum refineries contains a large number of compounds, most of which are hydrocarbons. In addition to the hydrocarbons, the effluent also contains grease (0.01 to 2%), sulphur (0–6%), cyanide (0.1 to 0.2%), suspended solids etc. (Khan 1995, Abdulbasher, 1985).

Phenols are by-products obtained during the refining process. The concentration of phenols in the waste-waters depends largely on the nature of the crude oil processed. Phenol when present in waste-waters not only leads to odour and taste problems but also poses a serious threat to fish and other aquatic organisms due to its highly toxic nature. Apart from this, some phenolic compounds also accelerate tumour formation leading to carcinogenicity. For these reasons, refinery waste-waters exceeding the limit of 0.05 mg/l of phenols are not permitted to be discharged into the main streams. In order to bring the concentrations of phenol within the permissible limit of the set standards, it becomes necessary to treat the refinery waste-water before it is discharged into the main stream.

For the removal of phenolic compounds from the industrial effluents, biological methods using single micro-organisms or a group of micro-organisms present in activated sludge have been used which utilize the organic compounds through a process called biodegradation (Rajakumar et al. 1991, Subhani et al. 1991). During biodegradation, the micro-organisms convert organic compounds into their inorganic forms which in turn serve as energy source or substrate for micro-organisms. The drawback of single bacteria is that it may not be able to fully biodegrade phenol and phenolic compounds due to non-availability of an array of enzymes responsible for complete biodegradation, wherein a microbial consortium proves to be better than a single bacterium for biodegradation because a number of enzymes present in different bacteria undergo co-metabolism. The micro-organisms present in the activated sludge have low efficiency because of suppression of specific bacteria present therein, thereby resulting in the inadequate and variable micro-flora and are not able to degrade the compounds of interest present in specific waste-waters. Another drawback of the conventional biological treatment method is that free microbial cells are unable to tolerate high concentrations of phenol present in petroleum refinery because of high toxicity of phenol on micro-organisms containing phenol degrading enzymes. Whereas, the advantages of the present invention over the above conventional methods envisage an effective and efficient removal of phenolic compounds from the waste-waters of petroleum refinery by selecting a blend of specialized micro-organisms from the source habitat which are capable of degrading them.

Though few micro-organisms have been immobilized on various supports to biodegrade phenol present in waste-waters, there are many drawbacks of the used supports as disclosed in the prior art. The supports are biodegradable, toxic, expensive, have low mechanical strength and have less surface area. Therefore, it is essential to develop microbial consortium, immobilized on a non-biodegradable, non-toxic, mechanically strong, having more surface area and economically cheaper support to enhance the biodegradability of phenol.

To overcome this problem, in the present invention, a defined microbial consortium is formulated as well as immobilized on non-biodegradable and economically cheaper support to achieve an effective as well as efficient biological treatment of phenolic waste-water of petroleum refinery. Immobilization of micro-organisms leads to a reduction in cell growth and protection of the microbial cells from the toxicant. Due to these reasons, immobilized cells offer a promising potential for an effective and efficient biological treatment of waste-waters. Immobilized bio-catalysts have also been used on an industrial scale for treating effluents containing phenolic compounds (Anselmo and Novail, 1992) as well as other toxicants (Wong et al, 1993 and Cijzen et al, 1988).

For solving the aforementioned problem, the applicants have realized that there exists a need to provide a process for an effective and efficient treatment of phenolic compounds present in petroleum refinery using microbial consortium immobilized on a non-biodegradable and economically cheaper support.

In the present invention, coconut fibre is used as a support for immobilization of microbial consortium having wider surface area of coconut fibres which enables adsorption of higher number of cells on the surface of the support which results in faster biodegradation of phenol. Coconut fibre as such is not easily biodegradable. Therefore, it has longer shelf life. This support is non-toxic to micro-organisms as well as is mechanically strong.

OBJECTS OF THE INVENTION

The main object of the present invention is to provide an immobilized microbial consortium and a process for the preparation of the said immobilized microbial consortium on a non-biodegradable and economically cheaper support for the treatment of phenolic waste-waters, which obviates the drawbacks as detailed above.

Another object of the present invention is to provide a process for the preparation of immobilized microbial consortium on non-toxic and mechanically strong support for the treatment of phenolic waste-waters.

Still another object of the present invention is to provide a process for the preparation of immobilized consortium on a support having wider surface area which enables the easy diffusion of oxygen as well as the nutrients which help in biodegradation of phenolic compounds.

SUMMARY OF THE INVENTION

The present invention relates to a process for the preparation of immobilized microbial consortium on coconut fibre for treatment of phenol present in petroleum refinery. Wider surface area of coconut fibres used for immobilization enables adsorption of higher number of cells on the surface of the support which results in faster biodegradation of phenol. Coconut fibre as such is not easily biodegradable. Therefore, it has a longer shelf life. The support is non toxic to micro-organisms as well as is mechanically strong.

DETAILED DESCRIPTION OF THE INVENTION

The composition provided according to the present invention contains bacteria consisting of:

| S.No. | Cultures | Accession No. | Prior art strains having characteristics similar to that of CBTCC No. |
|---|---|---|---|
| (a) | Aeromonas hydrophila | CBTCC/MICRO/10 | ATCC 7966 |
| (b) | Pseudomonas fluorescens | CBTCC/MICRO/11 | ATCC 13525 |
| (c) | Pseudomonas aeruginosa | CBTCC/MICRO/3 | ATCC 49622 |
| (d) | Bacillus circulans | CBTCC/MICRO/12 | ATCC 4513 |
| (e) | Yersinia enterocolitica | CBTCC/MICRO/4 | ATCC 27739 |
| (f) | Enterobacter cloaca | CBTCC/MICRO/1 | ATCC 29813 |
| (g) | Bacillus brevis | CBTCC/MICRO/13 | ATCC 8246 | which facilitate effective and efficient treatment of phenol present in effluent of petroleum refinery. Above micro-organisms are deposited at Centre for Biochemical Technology Culture Collection (CBTCC) designated as stated above and will be made available to public on request as per normal official procedures.

The main characteristic features of all the bacterial cultures used for the invention which are similar to ATCC cultures are given below:

Characteristic Features of *Aeromonas hydrophila* (CBTCC/Micro/10)

Gram-negative

Motile by a single polar flagellum

Metabolism of glucose is both respiratory and fermentative

Oxidase positive

Catalase positive

Ferments salicin, sucrose and mannitol

Produces hydrogen sulphide from cysteine

Characteristic Features of *Pseudomonas fluorescens* (CBTCC/Micro/11)

Gram negative, aerobic rod shaped bacteria

Have polar flagella

Metabolism is respiratory, never fermentative

Catalase positive

Produces pyoverdin

Gelatin liquefaction positive

Characteristic Features of *Pseudomonas aeruginosa* (CBTCC/Micro/3)

Gram negative, aerobic rod shaped bacteria

Have polar flagella

Metabolism is respiratory, never fermentative

Catalase positive

Oxidase positive

Denitrification positive

Characteristic Features of *Bacillus circulans* (CBTCC/Micro/12)

Gram-positive, rod shaped

Forms endospores, resistant to many adverse conditions

Aerobic or facultative anaerobic

Motile

Utilizes acetate

Hydrolyzes starch

Characteristic Features of *Yersinia enterocolitica* (CBTCC/Micro/4)

Gram-negative

Facultative anaerobic, having both respiratory and fermentative type of metabolism Oxidase negative Motile Produces acid from sucrose, cellobiose, sorbose and sorbitol Characteristic Features of *Enterobacter cloaca* (CBTCC/Micro /1)

Gram-negative straight rods

Motile by peritrichous flagella

Facultative anaerobe

Ferments glucose with production of acid and gas

KCN and gelatinase positive

Nitrate reductase positive

Decarboxylates ornithine and arginine

Characteristic Features of *Bacillus brevis* (CBTCC/Micro/13)

Gram-positive, rod shaped

Forms endospores, resistant to many adverse conditions

Aerobic or facultative anaerobic

Motile

Grows at pH 6–8

Degrades tyrosine

The composition may contain the bacteria, in a preferred embodiment of the invention, in uniform amounts. The bacterial cultures of the above composition are isolated from the effluent of petroleum refinery. Effluent of petroleum refinery is collected from Mathura oil refinery. Effluent is homogenized and suspended in nutrient broth medium containing 0.1 gm/l of phenol concentration. Incubation is carried out for 16–24 hours, cultures are plated on Mac Conkey's Agar. Colonies are mixed on a vortex mixer and all the cultures are isolated in pure cultures after several subcultures. The pure cultures are checked for the gram reactions. All the cultures are maintained as stock cultures.

The immobilization technique of formulated specialized microbial consortium of the present invention is carried out by inoculating the individual strains of the above mentioned bacteria separately in a nutrient broth. All the cultures are incubated preferably at 37° C. For approximately 24 hours in an incubator shaker. For gentle shaking, the incubator shaker is maintained at an appropriate rpm, preferably at 75 rpm. After sufficient growth is obtained, the bacterial cells from these individual cultures are taken in the required quantity and mixed for preparing the microbial consortium. The resultant microbial consortium is centrifuged at appropriate rpm, preferably at 10,000 rpm for a period of approximately 30 minutes. The resultant pellet is washed by dissolving in minimum quantity of phosphate buffer, 0.05 M, pH 6.8 and recentrifuged at appropriate rpm, preferably at 10,000 rpm for a period of approximately 30 minutes. During centrifugation the temperature is maintained preferably at 4° C. The resultant pellet was suspended in 2% of 25% (v/v) solution of glutaraldehyde for 2 hours at 100 rpm preferably at 35° C. to 37° C. The suspension of bacterial culture was centrifuged at appropriate rpm, preferably 10,000 rpm for a period of approximately 30 minutes. The resultant pellet was washed by dissolving in phosphate buffer, 0.05 M, pH 6.8 and centrifuging at approximate rpm, preferably at 10,000 rpm for a period of 30 minutes. The resultant pellet was suspended in 50 ml phosphate buffer, 0.05 M, pH 6.8. The support for immobilization was prepared by cutting the coconut fibre in small pieces having 1.5 inch length, 1.5 inch breadth and 1.0 inch diameter. The pre-treatment of pieces of coconut fibre was carried out by dipping in 1.0% v/v solution of $HgCl_2$ for a period of 5–10 minutes. The treated coconut fibre was removed and washed thoroughly with running tap water followed by triple distilled water. The obtained treated pieces of coconut fibres were dried in oven at around 40° C.–50° C. and sterilized by autoclaving at 15 lbs for 15 minutes. The resultant sterilized pieces of coconut fibre were dipped into the already prepared bacterial suspension in phosphate buffer, 0.05 M, pH 6.8 and incubated at appropriate temperature, preferably at 37° C. After proper incubation, the dipped pieces of coconut fibre were removed from the bacterial suspension. The obtained immobilized coconut fibres were air dried for 4–6 hours and stored at appropriate temperature preferably at 4° C. The immobilized pieces of coconut fibre so obtained are used for the efficient and effective treatment of synthetic phenol as well as phenol present in the industrial effluent of petroleum refinery.

Accordingly, the present invention provides a process for the preparation of microbial consortium immobilized on a non-biodegradable and economically cheaper support for the treatment of phenolic waste-waters which comprises of:

| S.No. | Cultures | Accession No. | Prior art strains having characteristics similar to that of CBTCC No. |
|---|---|---|---|
| (a) | Aeromonas hydrophila | CBTCC/MICRO/10 | ATCC 7966 |
| (b) | Pseudomonas fluorescens | CBTCC/MICRO/11 | ATCC 13525 |
| (c) | Pseudomonas aeruginosa | CBTCC/MICRO/3 | ATCC 49622 |
| (d) | Bacillus circulans | CBTCC/MICRO/12 | ATCC 4513 |
| (e) | Yersinia enterocolitica | CBTCC/MICRO/4 | ATCC 27739 |
| (f) | Enterobacter cloaca | CBTCC/MICRO/1 | ATCC 29813 |
| (g) | Bacillus brevis | CBTCC/MICRO/13 | ATCC 8246 |

The invention further provides for the preparation of immobilized microbial consortium which comprises:
(a) isolating a range of bacterial strains from effluent collected from petroleum refinery industry.
(b) culturing the said bacterial strain on nutrient media to get pure cultures.
(c) inoculating the said bacterial strains in nutrient broth, individually.
(d) incubating the said bacterial strains and growing the said incubated strains, individually;
(e) testing the phenol tolerance ability of the said grown bacterial cultures;
(f) selecting the said bacterial strains showing phenol tolerance limit for 0.2 to 0.4 gm/l;
(g) acclimatizing the said selected bacterial strains;
(h) mixing the said, acclimatized bacterial strains in equal proportions on the basis of optical density values to formulate a microbial consortium;
(i) centrifuging the said mixed bacterial strains to obtain pellet, washing the collected pellet with phosphate buffer, re-centrifuging, obtaining pellet;
(j) suspending the said pellet in 2% of 25% (v/v) solution of glutaraldehyde, a non-toxic cross-linking agent, for 2 hours at 75–100 rpm at a temperature ranging from 30–37+ C.;
(k) centrifuging the suspended bacterial cultures to obtain pellet, washing the obtained pellet with phosphate buffer 0.05–0.2 M, pH 6.8–7.2, re-centrifuging, obtained pellet;
(l) preparing the support by cutting the coconut fibre in small pieces;
(m) dipping the coconut fibre pieces in 0.05%–0.2% v/v solution of $HgCl_2$ for a period ranging from 5–10 minutes, washing thoroughly with triple distilled water;
(n) drying the coconut fibre pieces in oven and sterilizing;
(o) suspending the obtained pellet as in step (k) in phosphate buffer 0.05 M, pH 6.8, dipping the treated coconut fibre pieces from step (n);
(p) incubating the said bacterial suspension containing coconut fibres at 30–37° C. overnight;
(q) discarding the suspension, collecting the coconut fibre pieces on which micro-organisms are immobilized;
(r) air drying the coconut fibre pieces;
(s) storing the air dried coconut fibre pieces preferably at 1–4° C.;
(t) testing the air dried coconut fibre pieces for biodegradation of synthetic phenol;

In an embodiment of the present invention, the formulated microbial consortium is obtained by inoculating a suspension of the bacteria selected from a group consisting of *Aeromonas hydrophila, Pseudomonas fluorescens, Pseudomonas aeruginosa, Bacillus circulans, Yersinia enterocolitica, Enterobacter cloaca,* and *Bacillus brevis*.

In another embodiment of the present invention, the individual strains of above mentioned bacteria are inoculated separately in nutrient broth.

In yet another embodiment of the present invention, incubation is carried out by gentle agitation at approximately 75–100 rpm.

In one of the embodiment of the present invention, the growth of the incubated bacterial strains is carried out at temperature ranging between 30° C. to 37° C. For a period of 16–24 hours.

In another embodiment of the present invention, the grown, pure bacterial cultures were tested for phenol tolerance ability, by growing in phenol concentrations ranging from 0.2 to 1.0 g/l.

In an embodiment of the present invention, the said pure bacterial cultures tolerating phenol concentration up to 0.4 g/l were selected.

In a further embodiment of the present invention, the selected said bacterial strains were acclimatized to a higher concentration of phenol ranging from 0.5–2.0 g/l.

In still another embodiment of the present invention, the said individual, acclimatized bacterial strains are mixed in equal proportions.

In a further embodiment of the present invention, the resultant microbial consortium is centrifuged at appropriate rpm preferably at 8000–12000 rpm for a period of approximately 20–30 min.

In another embodiment of the present invention, the resultant pellet of microbial consortium is washed by dissolving in a appropriate quantity of phosphate buffer 0.05

M–0.1M, and pH 6.8–7.2 and re-centrifuging at an appropriate rpm in the range of 8000–12000 for a period of approximately 20–30 min., at a temperature ranging from 1 to 4° C.

In an embodiment of the present invention, the obtained pellet of microbial consortium suspended in 2% of 25% (v/v) solution of gluteraldehyde for 2 hours at 100 rpm preferably at 30° C. to 37° C.

In a further embodiment of the present invention, centrifuging the suspended microbial consortium to obtain the pellet, washing the obtained pellet with phosphate buffer 0.05 M–0.2M, and pH 6.8–7.2, recentrifuging, obtaining pellet.

In still another embodiment of the present invention, the support is prepared by cutting the coconut fibre in small pieces, dipping in 0.05%–0.2% v/v of $HgCl_2$ for 5–10 minutes, washing thoroughly in running tap water, again washing with triple distilled water, drying in oven and sterilizing the coconut fibre pieces at 15 lbs for 15–30 minutes. In another embodiment of the present invention, suspending the obtained pellet of microbial consortium in phosphate buffer, 0.05 M–0.2 M, pH 6.8–7.2.

In still another embodiment of the present invention, the treated coconut fibre pieces are dipped into the suspension of the microbial consortium.

In a further embodiment of the present invention, the inoculated coconut fibre pieces are incubated at a temperature ranging between 30° C. to 37° C. For a period of 16–24 hours.

In another embodiment of the present invention, the incubated coconut fibre pieces are separated from the suspension of microbial consortium.

In still another embodiment of the present invention, the separated coconut fibre pieces are air-dried for 4–6 hours and stored at temperature ranging between 1° C. to 4° C.

In a further embodiment of the present invention, the formulated microbial consortium, immobilized on coconut fibre pieces is used for the biodegradation of synthetic phenol ranging between 0.6–2.0 g/l.

The examples provided below are given by way of illustration of the invention and therefore, should not be construed to limit the scope of invention.

EXAMPLE I

The effluent from the petroleum refinery was collected three times at regular time intervals for the biological treatment. Physical parameters of the petroleum refinery effluent were analysed as shown in Table 1. The colour of the effluent was blackish and was giving unpleasant odour. The consistency of the collected effluent was thick and the range of pH was from 6.0 to 11.5. Simultaneously, the chemical parameters of the collected petroleum refinery effluent were also carried out as represented in Table2. The chemical parameters were analysed for oil and grease, chemical oxygen demand, cyanide, phenol and total solids. Among these, concentration of phenol is much higher and is most toxic to micro-organisms as compared to other parameters. Thus, phenol present in petroleum refinery was selected for the biological treatment.

EXAMPLE II

One loop of Aeromonas hydrophila, Pseudomonas fluorescens, Pseudomonas aeruginosa, Bacillus circulans, Yersinia enterocolitica, Enterobacter cloaca and Bacillus brevis, were inoculated in 1000 ml of nutrient broth individually. All the cultures were incubated at 37° C. For 24 hours in an incubater shaker at 75 rpm. After incubation, optical density was measured at 650 nm. Optical density of all the bacteria was maintained to 1.0, either by diluting or concentrating the bacterial suspension. All the bacterial suspensions were mixed thoroughly and centrifuged at 8,000 rpm for 30 min. at

TABLE 1

Physical parameters of oil refinery effluent

| Parameters analyzed | Characteristics of the effluent |
| --- | --- |
| Colour | Blackish |
| Odour | Unpleasant |
| Consistency | Thick |
| pH | 6.0–11.5 |

TABLE 2

Chemical parameters of oil refinery effluent

| Parameters analyzed | Values obtained, mg/l |
| --- | --- |
| Oil and grease | 0.102 |
| Chemical oxygen demand (COD) | 8361 ± 80 |
| Biological oxygen demand (BOD) | 3792 ± 108 |
| Cyanide | 12.98 ± 0.40 |
| Phenol | 2610 ± 132 |
| Total solids | 1403 ± 45 |

All values are mean of three readings

4° C. The pellet was washed by dissolving it in a small volume of phosphate buffer and re-centrifuged at 8,000 rpm for 30 minutes at 4° C.

The resultant pellet was suspended in 25 ml solution of 2% (v/v) glutaraldehyde for 2 hours. The cells were again centrifuged at 8,000 rpm for 30 minutes. The wet weight of the pellet was 0.7921 gm. The pellet was suspended in phosphate buffer and coconut fibre pieces of 1.5 inch length, 1.5 inch breadth and 1.0 inch diameter having 0.57 gm weight were inoculated in the suspension and incubated for 16–24 hours. After incubation, the immobilized coconut fibre pieces were taken out and air-dried. The left-over bacterial suspension was centrifuged at 8,000 rpm for 30 minutes. The wet weight of the pellet of left-over bacterial suspension was 0.6909 gm. The difference between the initial weight of bacterial suspension and weight of bacterial suspension after immobilization was 0.1012 gm. A total of 0.1012 gm cells were immobilized on three pieces of coconut fibre.

EXAMPLE III

One and a half loop of Aeromonas hydrophila, Pseudomonas fluorescens, Pseudomonas aeruginosa, Bacillus circulans, Yersinia enterocolitica, Enterobacter cloaca and Bacillus brevis, were inoculated in 1000 ml of nutrient broth individually. All the cultures were incubated at 37° C. For 24 hours in an incubator shaker at 100 rpm. After incubation, optical density was measured at 650 nm. Optical density of all the bacteria was maintained to 1.0, either by diluting or concentrating the bacterial suspension. All the bacterial suspensions were mixed thoroughly and centrifuged at 10,000 rpm for 20 minutes at 4° C. the pellet was washed by dissolving it in small volume of phosphate buffer and recentrifuged at 10,000 rpm for 20 minutes at 4° C.

The resultant pellet was suspended in 25 ml solution of 2% (v/v) gluteraldehyde for 2 hours. The cells were again centrifuged at 10,000 rpm for 20 minutes. The wet weight of the pellet was 1.0730 gm. The pellet was suspended in phosphate buffer and coconut fibre pieces of 1.5 inch length, 1.5 inch breadth and 1.0 inch diameter having 0.57 gm weight were inoculated in the suspension and incubated overnight. After incubation, the immobilized coconut fibre pieces were taken out and air dried. The left-over bacterial suspension was centrifuged at 10,000 rpm for 20 minutes at 4° C. The wet weight of the pellet of the left-over bacterial suspension was 0.9180 gm. The difference between the initial weight of bacterial suspension and weight of bacterial suspension after immobilization was 0.1550 gm. A total of 0.1550 gm cells were immobilized on three pieces of coconut fibre.

EXAMPLE IV

Two loops of *Aeromonas hydrophila*, *Pseudomonas fluorescens*, *Pseudomonas aeruginosa*, *Bacillus circulans*, *Yersinia enterocolitica*, *Enterobacter cloaca* and *Bacillus brevis*, were inoculated in 1000 ml of nutrient broth individually. All the cultures were incubated at 37° C. For 24 hours in an incubator shaker at 75 rpm. After incubation, optical density was measured at 650 nm. Optical density of all the bacteria was maintained to 1.0 either by diluting or concentrating the bacterial suspension. All the bacterial suspensions were mixed thoroughly and centrifuged at 12,000 rpm for 15 minutes at 4° C. The pellet was washed by dissolving it in small volume of phosphate buffer and recentrifuged at 10,000 rpm for 20 minutes at 4° C.

The resultant pellet was suspended in 25 ml solution of 2% of 25% (v/v) gluteraldehyde for 2 hours. The cells were again centrifuged at 12,000 rpm for 15 minutes at 4° C. The wet weight of the pellet was 1.2379 gm. The pellet was suspended in phosphate buffer and coconut, fibre pieces of 1.5 inch length, 1.5 inch breadth and 1.0 inch diameter, having 0.57 gm weight were inoculated in the suspension and incubated overnight. After incubation, the immobilized coconut fibre pieces were taken out and air-dried. The left-over bacterial suspension was centrifuged at 12,000 rpm for 15 minutes at 4° C. The wet weight of the pellet of the left-over bacterial suspension was 1.0368 gm. The difference between initial weight of bacterial suspension and weight of bacterial suspension after immobilization was 0.2011 gm. A total of 0.2011 gm cells were immobilized on three pieces of coconut fibre. Table 3 represents the wet weight of microbial consortium immobilized on coconut fibre.

EXAMPLE V

The immobilized pieces of coconut fibre containing 0.2011 gm cells of the formulated microbial consortium were used for the biodegradation of synthetic phenol in a concentration range of 0.6, 0.8, 1.0, 1.2, 1.4, 1.6, 1.8 and 2.0 gm/l.

Table 4 shows the percent biodegradation of synthetic phenol in a concentration range of 0.6, 0.8, 1.0, 1.2, 1.4, 1.6, 1.8, and 2.0 gm/l by microbial consortium immobilized on coconut fibre.

The immobilized microbial consortium was able to degrade 0.6 gm/l of phenol concentrations completely within 15 hours whereas 96% biodegradation of 0.8 gm/l of phenol concentration was observed by immobilized microbial consortium within 18 hours. This microbial consortium failed to degrade phenol concentration above 1.4 gm/l.

TABLE 3

Wet weight of microbial consortium immobilized on coconut fiber

| S.No | Wet weight of microbial consortium before immobilization (gm cells) | Wet weight of microbial consortium after immobilization (gm cells) | Wet weight of microbial consortium immobilized on coconut fiber (gm cells) |
|---|---|---|---|
| 1 | 0.7921 | 0.6909 | 0.1012 |
| 2 | 1.0730 | 0.9180 | 0.1550 |
| 3 | 1.2379 | 1.0368 | 0.2011 |

TABLE 4

Percent degradation of synthetic phenol by microbial consortium immobilized on coconut fiber

| Time (hours) | Concentrations of synthetic phenol(gm/l) | | | | | | | |
|---|---|---|---|---|---|---|---|---|
| | 0.6 | 0.8 | 1.0 | 1.2 | 1.4 | 1.6 | 1.8 | 2.0 |
| 3 | 31 | 24 | 19 | 12 | 7 | — | — | — |
| 6 | 47 | 38 | 30 | 28 | 13 | — | — | — |
| 9 | 59 | 52 | 44 | 35 | 21 | — | — | — |
| 12 | 72 | 65 | 51 | 43 | 21 | — | — | — |
| 15 | 100 | 87 | 70 | 61 | 21 | — | — | — |
| 18 | 100 | 96 | 84 | 73 | 21 | — | — | — |

EXAMPLE VI

The biodegradation of petroleum refinery effluent using microbial consortium immobilized on coconut fibre was carried out. The effluent was diluted three times to suppress the toxic effect of concentrated effluent which inhibits the biodegradation process. Three pieces of immobilized coconut fibres were used for the treatment of 500 ml effluent. The initial phenol concentration of the effluent was measured and the inoculated effluent was incubated at 37° C., 100 rpm. The treatment of effluent by immobilized microbial consortium was measured in terms of uptake of phenol at regular time intervals. Along with the experiments, a blank was also set up with all the test samples.

Table 5 represents percent residual phenol present in the effluent after biodegradation by microbial consortium immobilized on coconut fibre. The result revealed that around 70% phenol was left in the sample after 9 hours indicating 30% degradation of phenol.

EXAMPLE VII

Apart from non-biodegradable and economically cheaper support, i.e., coconut fibre, the well known commercially available support, i.e., calcium alginate was also used for the immobilization of formulated microbial consortium. The microbial consortium immobilized on both the supports namely coconut fibre and calcium alginate was used for the degradation of phenol present in effluent of petroleum refinery.

Table 6 represents the percent degradation of phenol by microbial consortium immobilized on coconut fibre and calcium alginate. Comparative analysis of the result of the biodegradation of phenol present in petroleum refinery effluent by microbial

TABLE 5

Percent residual phenol present in the effluent after biodegradation by microbial consortium immobilized on coconut fiber

| Time (Hours) | Percent residual phenol |
|---|---|
| 3 | 94 |
| 6 | 88 |
| 9 | 82 |
| 12 | 78 |
| 15 | 73 |
| 18 | 70 |
| 21 | 70 |

TABLE 6

Percent degradation of phenol present in petroleum Refinery by microbial consortium immobilized on coconut fiber and calcium alginate

| | Percent degradation of phenol | | |
|---|---|---|---|
| Time (Hours) | Microbial consortium immobilized on calcium-alginate (biodegradable) 0.9 g/l phenol in effluent (3 times diluted) | Microbial composition immobilized on coconut fiber (non-biogegradable) 0.9 g/l phenol in effluent (3 times diluted) | 0.9 g/l phenol (synthetic) |
| 3 | 3 | 6 | 21 |
| 6 | 8 | 12 | 33 |
| 9 | 15 | 18 | 48 |
| 12 | 19 | 22 | 60 |
| 15 | 22 | 27 | 81 |
| 18 | 26 | 30 | 93 |
| 21 | 26 | 30 | 93 | consortium immobilized on coconut fibre showed 30% degradation of phenol in 18 hours as compared to 26% when immobilized on calcium-alginate. On the other hand, synthetic phenol showed a degradation of 93% in 18 hours.

EXAMPLE VIII

The stability of the microbial consortium immobilized on coconut fibre was studied by storing the immobilized microbial consortium in different solutions and at different temperatures. Table 7 represents the stability study of microbial consortium immobilized on coconut fibre stored in different solutions, triple distilled water and phosphate buffer at different temperatures (4° C., 15° C., 25° C. and 37° C.).

The result of the stability study of microbial consortium immobilized on coconut fibre revealed that the immobilized microbial consortium remained stable for 120 days at 4° C. and 45 days at 15° C. when stored in phosphate buffer solutions. At 25° C., the immobilized microbial consortium remained stable for 30 days in phosphate buffer solution. The stability of the immobilized microbial consortium at 37° C. was 15 days only when stored in phosphate buffer solution. The immobilized micro-organisms stored in triple distilled water were less stable.

EXAMPLE IX

The viability of the immobilized microbial consortium was also checked at different temperatures stored in phosphate buffer, 0.05 M, pH 6.8.

Table 8 represents viability of microbial consortium immobilized on coconut fibre stored in phosphate buffer, 0.05 M, pH 6.8 at different temperatures.

TABLE 7

Stability of micro-organisms immobilized on coconut fiber stored in different solutions at different temperature

| | Temperature | | | | | | | |
|---|---|---|---|---|---|---|---|---|
| | 4° C. | | 15° C. | | 25° C. | | 37° C. | |
| Time (Days) | T.D.W. | PO₄ | T.D.W. | PO₄ | T.D.W. | PO₄ | T.D.W. | PO₄ |
| 15 | ++ | +++ | ++ | +++ | + | +++ | + | +++ |
| 30 | + | +++ | + | +++ | + | +++ | − | ++ |
| 45 | + | +++ | + | +++ | − | ++ | − | + |
| 60 | − | +++ | − | ++ | − | + | − | + |
| 90 | − | +++ | − | + | − | + | − | − |
| 120 | − | +++ | − | − | − | − | − | − |
| 150 | − | ++ | − | − | − | − | − | − |
| 180 | − | ++ | − | − | − | − | − | − |
| 210 | − | + | − | − | − | − | − | − |
| 240 | − | + | − | − | − | − | − | − |
| 270 | − | − | − | − | − | − | − | − |
| 300 | − | − | − | − | − | − | − | − |
| 330 | − | − | − | − | − | − | − | − |
| 360 | − | − | − | − | − | − | − | − |

+++ Stable
++ Less stable
+ Very less stable
− Unstable

TABLE 8

Viability of micro-organisms immobilizod oil coconut fiber
stored in phosphate buffer, 0.05 M, at different temperature

| Time | Temperature. | | | |
|---|---|---|---|---|
| (Days) | 4° C. | 15° C. | 25° C. | 37° C. |
| 15 | +++ | +++ | +++ | +++ |
| 30 | +++ | +++ | +++ | ++ |
| 45 | +++ | +++ | ++ | + |
| 60 | +++ | ++ | + | + |
| 90 | +++ | + | – | – |
| 120 | +++ | + | – | – |
| 150 | ++ | – | – | – |
| 180 | ++ | – | – | – |
| 210 | + | – | – | – |
| 240 | + | – | – | – |
| 270 | – | – | – | – |
| 300 | – | – | – | – |
| 330 | – | – | – | – |
| 360 | – | – | – | – |

+++ Viable
++ Less viable
+ Very less viable
– Non-viable

The results of viability study of the immobilized microbial consortium revealed that, at 4° C. the immobilized microbial consortium remained viable up to 120 days. At 15° C. the immobilized microbial consortium remained viable for 45 days, whereas, at 25° C. and 37° C., the viability of the immobilized microbial consortium decreased to 30 days and 15 days, respectively.

From examples I to IX explained above, it is clear that biodegradation of different concentrations of phenol using microbial consortium immobilized on coconut fibre is faster.

It is also clear from example VII that the support, i.e., coconut fibres, used for the immobilization is a better support than the well known support, i.e., calcium-alginate.

Advantages

1. The formulated microbial consortium acts synergistically for the effective degradation of phenol present in petroleum refinery effluent and is novel for this application. The formulated microbial consortium contains metabolically diverse micro-organisms which complement each other compensating for any physiological deficiencies in that particular species. With a better understanding of the interactions within such microbial consortium, it has been possible to manipulate them and harness their activities to technological advantages.
2. The support used for the immobilization of microbial consortium on coconut fibre is mechanically strong.
3. It is economically cheaper.
4. Coconut fibres are non-toxic to the micro-organisms used for the immobilization.
5. The fibres of coconut being rough, provide more surface area for the adsorption of the micro-organisms.
6. The support has appropriate porosity for easy transfer of oxygen as well as the nutrients.

We claim:

1. A formulated microbial consortium immobilized on coconut fibre pieces comprising a synergistic mixture of the following isolated bacterial strains present in equal proportions for the biodegradation of synthetic phenol as well as phenol present in effluent of petroleum refinery, using the consortium comprising of:

| S.No. | Cultures | Accession No. | Prior art strains having characteristics similar to that of CBTCC No. |
|---|---|---|---|
| (a) | Aeromonas hydrophila | CBTCC/MICRO/10 | ATCC 7966 | wherein the Aeromonas hydrophila is gram negative, oxidase positive, catalase positive, motile by a single polar flagellum, produces hydrogen sulphide from cysteine, ferments salicin, sucrose and mannitol, and metabolizes glucose by respiration and fermentation;

| (b) | Pseudomonas fluorescens | CBTCC/MICRO/11 | ATCC 13525 | wherein the Pseudomonas fluorescens is gram negative, catalase positive, gelatin liquefaction positive, has a polar flagella, has an aerobic rod shape, produces pyoverdin, and metabolizes by respiratory and never by fermentation;

| (c) | Pseudomonas aeruginosa | CBTCC/MICRO/3 | ATCC 49622 | wherein Pseudomonas aeruginosa is gram negative, oxidase positive, catalase positive, denitrification positive, has a polar flagella, has an aerobic rod shape, and the metabolizes by respiration and never by fermentation;

| (d) | Bacillus circulans | CBTCC/MICRO/12 | ATCC 4513 | wherein the Bacillus circulans is gram positive, motile, has a rod shape, forms endospores, utilizes acetate, hydrolyzes starch, and is aerobic or facultative anaerobic;

| (e) | Yersinia enterocolitica | CBTCC/MICRO/4 | ATCC 27739 | wherein the Yersinia enterocolitica is gram negative, oxidase negative, motile, produces acid from sucrose, cellobiose, sorbose and sorbitol, and faculative anaerobic, and metabolizes by respiration and fermentation;

| (f) | Enterobacter cloaca | CBTCC/MICRO/1 | ATCC 29813 | wherein the Enterobacter cloaca is gram negative, KCN and gelatinase positive, nitrate reducase positive, motile by peritrichous flagella, has straight rods, faculative anaerobe, ferments glucose with the production of acid and gas, and decarboxylates ornithine and arginine; and

| (g) | Bacillus brevis | CBTCC/MICRO/13 | ATCC 8246 | wherein the Bacillus brevis is gram positive, motile, rod shaped forms endospores, aerobic of faculative anaerobic, grows at a pH of 6–8 and degrades tyrosine;

2. A process for the preparation of the immobilized microbial consortium which comprises:
   (a) isolating a range of bacterial strains from effluent collected from petroleum refinery industry;
   (b) culturing the said bacterial strains on nutrient media to get pure cultures;
   (c) inoculating the said bacterial strains in nutrient broth, individually;
   (d) incubating the said bacterial strains and growing the said incubated strains, individually;
   (e) testing the phenol tolerance ability of the said pure bacterial cultures;
   (f) selecting the said bacterial strains showing phenol tolerance limit for 0.2 to 0.4 gm/l;
   (g) acclimatizing the selected said bacterial strains;
   (h) mixing the said acclimatized bacterial strains in equal proportions on the basis of optical density values to formulate a microbial consortium;
   (i) centrifuging the said mixed bacterial strains to obtain pellet, washing the collected pellet with phosphate buffer, re-centrifuging, obtaining pellet;
   (j) suspending the said pellet in 2% of 25% (v/v) solution of glutaraldehyde, a non-toxic cross-linking agent, for 2 hours at 100 rpm at a temperature ranging from 30–37° C.;
   (k) centrifuging the suspended bacterial cultures to obtain pellet, washing the obtained pellet with phosphate buffer 0.05–0.2 M, pH 6.8–7.2, re-centrifuging, obtaining pellet;
   (l) preparing the support by cutting the coconut fibre in small pieces;

(m) dipping the coconut fibre pieces in 0.05%–0.2% v/v solution of $HgCl_2$ for a period ranging from 5–10 minutes, washing thoroughly with triple distilled water;

(n) drying the coconut fibre pieces in oven and sterilizing;

(o) suspending the obtained pellet as in step (k) in phosphate buffer 0.05 M, pH 6.8, dipping the treated coconut fibre pieces from step (n);

(p) incubating the said bacterial suspension containing coconut fibres at 30–37° C. overnight;

(q) discarding the suspension, collecting the coconut fibre pieces on which micro-organisms are immobilized;

(r) air drying the coconut fibre pieces;

(s) storing the air dried coconut fibre pieces preferably at 1–4° C.;

(t) testing the air dried coconut fibre pieces for biodegradation of synthetic phenol.

3. A process as claimed in claim 2, wherein the individual strains of the above mentioned bacterial strains are inoculated separately in 500–1000 ml nutrient broth.

4. A process as claimed in claim 2, wherein the incubation of bacterial strains is carried out by gentle agitation at approximately 75–100 rpm.

5. A process as claimed in claim 2, wherein the growth of incubated bacterial strains is carried out at a temperature ranging between 30° C.–37° C for a period of 16–24 hours.

6. A process as claimed in claim 2 (g), wherein the selected bacterial strains are acclimatized in the phenol concentration ranging from 0.5–2.0 gm/l.

7. A process as claimed in claim 2, wherein the resultant microbial consortium is centrifuged at 8,000 to 12,000 rpm for a period of approximately 15 to 30 minutes.

8. A process as claimed in claim 2(i), wherein the resultant pellet is washed by dissolving in an appropriate quantity of phosphate buffer 0.05 M–0.2 M, pH 6.8–7.2; recentrifuging at an appropriate rpm in the range of 8,000 to 12,000 rpm for a period of approximately 15 to 30 minutes at a temperature of 4° C.

9. A process as claimed in claim 2 (l), wherein the support used for immobilization is prepared by cutting the pieces of coconut fibre in the range of 0.5–1.0 inch length, 0.5–1.5 inch breadth and 1.0 inch diameter.

10. A process as claimed in claim 2(n), wherein the coconut fibre used as support is dried in oven at a temperature ranging from 25–37° C. and sterilized at 15 lbs for about 15 to 30 minutes.

11. A process as claimed in claim 2 (q), wherein the immobilized coconut fibre piece is collected and air dried for a period of approximately 4–6 hours.

12. A process as claimed in claim 2 (t), wherein the immobilized coconut fibre pieces are used for the biodegradation of synthetic phenol ranging from 0.6 to 2.0 gm/l.

13. A process as claimed in claim 2 wherein the immobilized coconut fibre pieces are used for the treatment of phenol effluent present in petroleum refinery.

* * * * *